United States Patent [19]
Pollock et al.

[11] Patent Number: 5,985,623
[45] Date of Patent: *Nov. 16, 1999

[54] DNA SEGMENTS AND METHODS FOR INCREASING POLYSACCHARIDE PRODUCTION

[75] Inventors: Thomas J. Pollock; Motohide Yamazaki, both of San Diego; Linda Thorne, Palomar; Marcia Mikolajczak, Encinitas; Richard W. Armentrout, La Jolla, all of Calif.

[73] Assignees: Shin-Etsu Bio, Inc., San Diego, Calif.; Shin-Etsu Chemical Co., Ltd., Tokyo, Japan

[*] Notice: This patent is subject to a terminal disclaimer.

[21] Appl. No.: 08/377,440

[22] Filed: Jan. 24, 1995

[51] Int. Cl.$^6$ .............................. C12P 19/04; C12N 1/20; C07H 21/04

[52] U.S. Cl. .................. 435/101; 435/104; 435/252.3; 435/822; 536/23.2

[58] Field of Search ................. 536/23.2; 435/252.3, 435/101, 104, 172.1

[56] References Cited

U.S. PATENT DOCUMENTS

| | | | |
|---|---|---|---|
| 3,960,832 | 6/1976 | Kang et al. | 260/209 |
| 4,326,053 | 4/1982 | Kang et al. | 536/1 |
| 4,342,866 | 8/1982 | Kang et al. | 536/119 |
| 4,401,760 | 8/1983 | Peik et al. | 435/101 |
| 4,529,797 | 7/1985 | Peik et al. | 536/123 |
| 4,535,153 | 8/1985 | Kang et al. | 536/123 |
| 5,338,841 | 8/1994 | Pollock et al. | 536/23.7 |
| 5,342,773 | 8/1994 | Thorne et al. | 435/200 |

FOREIGN PATENT DOCUMENTS 0209277  1/1987  European Pat. Off. .

OTHER PUBLICATIONS

Martin, M.O. (1994) "Synthesis of commercially valuable bacterial polymers: impact of molecular genetics" Research in Microbiology. 145(2):93–97, 1994.

Fialho, A.M. et al. (1991) "Conjugal transfer of recombinant plasmids into gellan gum–producing and non–producing variants of Pseudomonas elodea ATCC 31461" Lett. in Appl. Microbiol. 12(3):85–87, Mar. 1991.

Ditta, et al "Broad host range DNA cloning system for Gram–negative bacteria: Construction of a gene bank of Rhizobium meliloti" Proc. Natl. Acad. Sci. USA Vo.77, No. 12, pp. 7347–7351, Dec. 1980.

Birnboim et al, "A rapid alkaline extraction procedure for screening recombinant plasmid DNA" Nucleic Acids Research, vol. 7, No. 6 1979, pp. 1513–1523.

Loftus et al, "A Rapid Method for Cosmid Cloning" 172 BioTechniques, vol. 12, No. 2 (1992).

Yabuuchi et al., "Proposals of Sphingomonas paucimobilis gen. nov. and comb. nov., . . . " Microbiol. Immunol. vol. 34 (2), 99–119, 1990.

Pollock et al "Mechanism of Bacitracin Resistance in Gram–Negative Bacteria That Synthesize Expolysaccharides" Journal of Bacteriology, vol. 176, No. 20, Oct. 1994. p 6229–6237.

Pollock, "Gellan–related polysaccharides and the genus Sphingomonas" J.of General Microbiology (1993) 139, 1939–1945.

Thorne, et al "Clustering of Mutations Blocking Synthesis of Xanthana Gum by *Xanthomonas campestris*" Journal of Bacteriology, Aug. 1987, vol. 169, No. 8, P. 3593–3600.

Thorne, et al "Direct utilization of lactose in clarified cheese whey for xanthan gum synthesis by *Xanthomonas campestris*" Journal of Industrial Microbiology, 3 (1988) 321–328.

Harding, et al "Isolation of Genes Essential For The Biosynthesis of Gellan Gum" FASEB Journal, vol. 7, No. 7.

*Primary Examiner*—Robert A. Wax
*Attorney, Agent, or Firm*—McAulay Nissen Goldberg Kiel & Hand, LLP

[57] ABSTRACT

The present invention relates to DNA segments isolated from Sphingomonas sp. and involved in the biosynthetic production of sphingan polysaccharides to increase the production of the polysaccharide in engineered microorganisms. The present invention also relates to methods of engineering strains of Sphingomonas to produce bacteria which are hyperproducers of sphingan, methods of identifying and utilizing DNA fragments useful to enhance production of sphingan in bacteria and the hyperproducer bacteria.

10 Claims, 7 Drawing Sheets

DNA Sequence of spsB Gene

```
AGCCCGAATG.CTGCATCCGC.GAAGTGACTT.TCGCCAAAGC.AGCTATAGGA    50
TGGCCCGGGG.CTTGATTGCC.GCCGTGCGAT.CAGCATAAGC.GATCCATGGT   100
CGCCAAAATC.TGTCATCCTT.GGTAACAATC.ATGCAGCCGC.TAAGGAAGAT   150
GTGCACGTCT.GACGATGCTT.TCTTCCGCAC.CCCATGCGCC.GCTGACTCTG   200
GTAGATTGAC.CGTGGCCTCC.ATTGCTCATC.GTCTCGAAAA.AGGACCCTCT   250
GGTCGCCGCG.CGGACTTCCG.GGAATCGATT.TGTCCCGTTA.TAGTGCAATG   300
CAACAGGCCG.AATCGGCCGC.TGTCAGCGTG.CACAATCCGT.TGAGGGAGCC   350
CGACGAGGCA.ATGAACGCTT.TTGAAGCACA.GCGCGCCTTT.GAGGAGCAGC   400
TCCGGGCCCA.TGCCCGTTCT.GCCCCAGCG.CCGCACCCAT.GCTGCGACGT    450
TCCACGATCC.GCATGATCCT.CTACACCGAA.TTGCTGTTGC.TCGACAGCAT   500
CGCAATTCTA.CTGGGGTTCT.ACATCGCGGC.CTGCTCGCGC.GACGGCAACT   550
GGCTGTCCCT.TGCGGGCGTC.AATGTCGGCA.TCTTCCTCCT.GCCGATCACG   600
CTCGGCACCG.CGCTCGCCAG.CGGCACCTAT.TCGCTGAGCT.GCCTGCGCTA   650
CCCGGTCAGC.GGGGTGAAGA.GCATCTTCTC.GGCGTTCTTC.TTCTCGGTGT   700
TCATCGTGCT.GCTGGGCAGC.TACCTGCTCA.CCGCGGAGCT.GCCGCTGTCG   750
CGCCTGCAGC.TCGGCGAGGG.CGTGCTCCTG.GCGCTCAGCC.TGGTGACGAT   800
CTGCCGCCTT.GGCTTCCGCT.GGCACGTTCG.TGCGCTGACA.CGCGGCACGC   850
TGCTCGACGA.GCTGGTGATC.GTCGACGGCG.TTGCCCTGGA.GGTCGCGAGC   900
GGCGCGGTCG.CGCTCGATGC.GCGCATCATC.AACCTCACGC.CCAACCCGCG   950
CGATCCGCAG.ATGCTGCATC.GCCTCGGCAC.CACCGTGGTG.GGCTTCGACC  1000
GGGTCGTCGT.CGCCTGCACC.GAGGAGCACC.GGGCAGTATG.GGCGCTGCTG  1050
CTCAAGGGCA.TGAACATCAA.GGGCGAGATC.CTCGTCCCCC.AGTTCAACGC  1100
GCTGGGCGCG.ATCGGCGTCG.ACTCCTATGA.GGGCAAGGAC.ACGCTGGTCG  1150
TGTCCCAGGG.CCCGCTCAAC.ATGCCGAACC.GCGCAAAGAA.GCGGGCGCTC  1200
GATCTGCTCA.TCACCGTCCC.CGCGCTGGTC.GCGCTGGCGC.CGCTGATGAT  1250
CGTGGTCGCG.ATCCTGATCA.AGCTGGAGAG.CCCCGGCCCC.GTCTTCTTCG  1300
CACAGGACCG.CGTCGGCCGC.GGCAACCGAC.TGTTCAAGAT.CCTCAAGTTC  1350
CGCTCGATGC.GCGTTGCGCT.CTGCGATGCG.AACGGCAACG.TCTCGGCCAG  1400
CCGCGATGAC.GATCGCATCA.CCAAGGTAGG.CCGGATCATC.CGCAAGACCA  1450
GCATCGACGA.GCTGCCGCAG.CTGCTCAACG.TGCTGCGCGG.CGACATGAGC  1500
GTCGTCGGCC.CGCGCCCGCA.CGCACTCGGG.TCGCGCGCCG.CCAACCATCT  1550
CTTCTGGGAA.ATCGACGAGC.GCTACTGGCA.CCGCCACACG.CTCAAGCCGG  1600
GCATGACGGG.CCTCGCGCAG.ATCCGCGGCT.TCCGCGGCGC.GACCGATCGC  1650
CGCGTCGATC.TCACCAATCG.CCTGCAGGCG.GACATGGAGT.ATATCGACGG  1700
CTGGGACATC.TGGCGGACG.TCACCATCCT.GTTCAAGACG.CTGCGCGTGA   1750
TCGTGCACTC.CAACGCCTTC.TGATCGCGGA.GGGGAGCAAC.GCGAGCACCG  1800
CTTGGTGCAA.GAGCATTGAC.ATCCGCCCTG.CTTCTGCATT.TGTCATTTTA  1850
TCATTGTCGT.TGCGGGCCCG.CCCGCGCCAT.GGGGGATTTT.GAATGAAGGG  1900
TATCATCCTT.GCGGGGGGCA.GCGGCACGCG.CCTCTACCCC.GCAACGCTGT  1950
```

Fig. 4

Deduced Amino Acid Sequence of the SpsB Protein

MNAFEAQRAFEEQLRAHARSAPSAAPMLRRSTIRMILYTELLLLDSIAIL
LGFYIAACSRDGNWLSLAGVNVGIFLLPITLGTALASGTYSLSCLRYPVS
GVKSIFSAFFFSVFIVLLGSYLLTAELPLSRLQLGEGVLLALSLVTICRL
GFRWHVRALTRGTLLDELVIVDGVALEVASGAVALDARIINLTPNPRDPQ
MLHRLGTTVVGFDRVVVACTEEHRAVWALLLKGMNIKGEILVPQFNALGA
IGVDSYEGKDTLVVSQGPLNMPNRAKKRALDLLITVPALVALAPLMIVVA
ILIKLESPGPVFFAQDRVGRGNRLFKILKFRSMRVALCDANGNVSASRDD
DRITKVGRIIRKTSIDELPQLLNVLRGDMSVVGPRPHALGSRAANHLFWE
IDERYWHRHTLKPGMTGLAQIRGFRGATDRRVDLTNRLQADMEYIDGWDI
WRDVTILFKTLRVIVHSNAF

Fig. 5

| POLYSACCHARIDE | STRUCTURE |
|---|---|

Gellan

```
                                                                L-Glyceric
                                                                    1
                                                                    ↓
                                                                    2
        →4)-β-D-GlcA-(1→4)-β-D-Glc-(1→4)α-L-Rha-(1→3)-β-D-Glc-(1→
```

Sphingan S-88
```
        →4-β-D-GlcA-(1→4)-β-D-Glc-(1→4)-α-L-Rha-(1→3)-β-D-Glc-(1→
                            3             or
                            ↑             Man
                            1
                          α-L-Rha
```

Welan
```
        →4)-β-D-GlcA-(1→4)-β-D-Glc-(1→4)-α-L-Rha-(1→3)-β-D-Glc-(1→
                            3
                            ↑
                            1
                    α-L-Rha(2/3) or Man (1/3)
```

Sphingan NW11   →4)-β-D-GlcA-(1→4)-β-D-Glc-(1→4)-α-L-Man-(1→3)-β-D-Glc-(1→

Sphingan S-198
```
        →4)-β-D-GlcA-(1→4)-β-D-Glc-(1→4)-α-L-Rha-(1→3)-β-D-Glc-(1→
                                    or          3
                                    Man         ↑
                                                1
                                    (1/2) α-L-Rha
```

S-657
```
        →4)-β-D-GlcA-(1→4)-β-D-Glc-(1→4)-α-L-Rha-(1→3)-β-D-Glc-(1→
                            3
                            ↑
                            1
                    α-L-Rha-(1→4)-α-L-Rha
``` rhamsan S-194
```
        →4)-β-D-GlcA-(1→4)-β-D-Glc-(1→4)-α-L-Rha-(1→3)-β-D-Glc-(1→
                                                        6
                                                        ↑
                                                        1
                                    α-D-Glc-(1→6)-α-D-Glc
```

DNA SEGMENTS AND METHODS FOR INCREASING POLYSACCHARIDE PRODUCTION

FIELD OF THE INVENTION

The present invention relates to DNA sequences and fragments, thereof, which are involved in the biosynthetic production of sphingan polysaccharides of and isolated from Sphingomonas sp. The isolated DNA fragments may be inserted into the same or different strains of Sphingomonas sp. or related bacteria in multiple copies to increase polysaccharide, preferably sphingan production. The engineered bacteria containing exogenous DNA produce significantly greater amounts of polysaccharide compared to non-engineered bacteria under identical fermentation conditions. The present invention also relates to methods of engineering strains of Sphingomonas sp. and other related bacteria to be hyperproducers of polysaccharide as well as the engineered bacteria. Methods of identifying and isolating DNA sequences useful for increasing the production of sphingan polysaccharides in Sphingomonas sp. are also described.

BACKGROUND OF THE INVENTION

A number of microorganisms produce extracellular polysaccharides, also known as exopolysaccharides or EPS. Of the exopolysaccharides, xanthan gum and a group of polysaccharides known as "sphingans" are included. "Sphingans" are produced by gram-negative bacteria of the genus Sphingomonas.

Xanthomonas campestris is a gram-negative bacterium which constitutively produces an exopolysaccharide, xanthan gum, in large amounts. Jeanes, et al., *J. Appl. Polymer Sci.*, 5,519–526 (1961). The biosynthesis of xanthan gum has been studied in considerable detail because of its commercial importance. Recently, another bacterial exopolysaccharide, gellan, was developed as a gelling agent. Gellan is a member of a family of related polysaccharides which includes S-88 (See, Kang and Veeder, U.S. Pat. No. 4,535,153); welan (See, Kang and Veeder, U.S. Pat. No. 4,342,866); NW11 (See, Robison and Stipanovic, U.S. Pat. No. 4,874,044); rhamsan (See, Peik, et al., U.S. Pat. No. 4,401,760); S-198 (See, Peik, et al. U.S. Pat. No. 4,529,797); S-657 (See, Peik, et al., Eur. Patent Application 209277A1); and heteropolysaccharide-7 (See, Kang and McNeely, U.S. Pat. No. 4,342,866). This group of polysaccharides is referred to as "spiingans" because they are all produced by gram-negative bacteria belonging to the genus Sphingomonas.

The above documents include several patents which relate to sphingan polysaccharide compositions. None of the patents remotely relates to the subject matter of the instant invention.

| Strain | Sphingan | Patent Number |
| --- | --- | --- |
| ATCC 31461 S60 | gellan S-60 | 4,326,053 |
| ATCC31554 S88 | S-88 | 4,535,153 |
| ATCC31853 S198 | S-198 | 4,529,797 |
| ATCC21423 S7 | S-7 | 3,960,832 |
| ATCC31555 S130 | welan S-130 | 4,342,866 |
| ATCC31961 S193 | rhamsan S-194 | 4,401,760 |
| ATCC53159 S-657 | S-657 | EurApp 0209277 |
| ATCC53272 NW11 | NW-11 | 4,874,044 |

The chemical structures of the sphingan polysaccharides are all somewhat related. The main chain of each sphingan consists of a related sequence of four sugars-D-glucose, D-glucuronic acid, L-mannose and L-rhamnose. Polysaccharide members of the sphingan group are distinguishable from each other by virtue of the carbohydrates which comprise the polymer backbone (main chain) and the sidechains. The sphingan carbohydrates may contain carbohydrate side chains and acetyl or pyruvyl groups attached to carbohydrates on the polymer backbone.

Various sphingans are useful as specialty polymers and as additives in textile applications, foods, cosmetics, paper, paint, cements, e.g. as viscosity modifiers, in various other coating applications, and as adhesives and additives to petroleum products and specialty chemicals.

The focus of initial studies which culminated in the present invention was the first step in the biosynthesis of a representative sphingan polysaccharide, S-88. This sphingan is biosynthesized by Sphingomonas strain S88. Prior to the instant invention, it was known that some, but not all, bacterial polysaccharide biosynthesis of other than sphingans utilize an isoprenylphosphate carrier. For example, in the case of xanthan gum biosynthesis by *X. campestris*, since the main chain of xanthan gum contains only glucose, the first synthetic step is likely the transfer of glucose-phosphate from UDP-glucose to a C55-isoprenylphosphate (IP) carrier. With cell-free incorporation assays, Jelpi, et al., *FEBS Lett.*, 130, 253 (1982) and *J. Bacteriol.*, 175, 2490 ((1993), confirmed that glucose, followed by a second glucose, and then mannose, glucuronic acid and mannose are added sequentially to carrier IP to assemble the repeating unit of xanthan gum. Quite similarly, the repeating subunit of colanic acid in *Escherichia coli* is assembled by first transferring glucose-P to IP. Johnson and Wilson, *J. Bacteriol.*, 129, 225 (1977). By contrast, in the case of the synthesis of succinoglycan polysaccharides by *Rhizobium meliloti*, a galactose-P is transferred first to IP. See, Tolmasky, et al., *J. Biol. Chem.*, 257, 6751 (1982). Isoprenyl carriers, however, are not involved in the synthesis of dextran or levan polysaccharides, and the role of isoprenyl carriers in alginate synthesis is unknown.

Prior to the investigation which led to the present invention, the importance of the role of the carrier in the complex kinetics of the biosynthesis of polysaccharides was not known. In addition, it was not known what role the isoprenylphosphate carrier might play in the overall synthesis of sphingan polysaccharides in Sphingomonas bacteria.

Previously, genetic complementation tests have shown that a special class of mutations in *X. campestris* which are simultaneously Bac$^r$ and Gum$^-$ (bacitracin-resistant and xanthan gum-negative) map within the gumD gene which is required for transferring glucose-P from UDP-Glc to IP to give Glc-PPI. Pollock, et al., 1994, *J. Bacteriol*, vol. 176, pp. 6229–6237, Vanderslice, et al., "Genetic Engineering of polysaccharide structure in *Xanthomonas campestris*", p. 145–156, in V. Crescenzi, et al., Biomedical and Biotechnological Advances in Industrial Polysaccharides, Gordon and Breach Science Publishers, New York and N. E. Harding and Y. N. Patel, 1993, *Faseb Journal*, Vol. 7, Number 7. The latter reference discloses fragments of DNA that can restore synthesis of sphingan S-60 to non-producing mutants, but gives no indication of increased synthesis relative to the wild-type strain. Earlier experimentation also showed that the wild type gumD gene of *X. campestris* could restore synthesis of sphingans in analogous Bac$^r$ Sps$^-$ (sphingan polysaccharide-negative) mutants of Sphingomonas strains S88 and NW 11. It was suggested that Bac$^r$ Sps$^-$ Sphingomonas mutants also appeared to be blocked in the transfer of glucose-P to IP.

OBJECTS OF THE INVENTION

It is an object of the present invention to provide DNA segments which are isolated from Sphingomonas sp. and may be used to enhance the production of sphingan polysaccharide in a number of microorganisms, and in particular, a number of strains of Sphingomonas.

It is also an object of the present invention to provide hyperproducer strains of microorganisms, and in particular, a number of strains of Sphingomonas which will produce significantly more sphingan polysaccharide than non-engineered strains.

It is a further object of the present invention to provide a method for producing strains of microorganisms, and in particular, strains of Sphingomonas sp. which are hyperproducers of sphingan polysaccharide.

It is an additional object of the present invention to provide a method for isolating DNA segments which may be inserted into Sphingomonas strains so that the resulting engineered microorganism becomes a hyperproducer of sphingan polysaccharide.

These and other objectives of the present invention may be readily gleaned from the description of the invention which follows.

SUMMARY OF THE INVENTION

In the present invention, sequences of DNA as segments or fragments are isolated from sphingan-producing bacteria, generally from Sphingomonas strains. The resulting genetic material is cloned, incorporated as multiple copies into sphingan-producing or non-producing mutants of Sphingomonas or related bacteria. These DNA sequences have proved useful in restoring sphingan production in mutant bacteria which do not produce sphingan. Moreover, unexpectedly it has been found that the restoration of sphingan production in these mutants is coupled with production of amounts of sphingan which is significantly greater than the production expected from wild type strains which produce Sphingan.

We have unexpectedly discovered that DNA segments or fragments which are isolated from one Sphingomonas strain may be inserted as multiple copies into sphingan-producing or mutant non-producing bacteria of the same strain or different strains of Sphingomonas with the resultant engineered bacterium becoming a hyperproducer of sphingan. This is particularly unexpected inasmuch as the DNA segments or fragments isolated from, for example, Sphingomonas S60 and inserted into Sphingomonas S88 wild type or nonmucoid mutants will produce an engineered hyperproducer of S-88 sphingan which is generally not contaminated with S-60 sphingan. This complementation may be rather broadly applied across various strains of Sphingomonas (interstrain complementation) and even to the production of xanthan gum in *Xanthomonas campestris* (intergeneric complementation).

We have further discovered a method for producing engineered hyperproducing Sphingomonas bacteria which incorporate the DNA segments or fragments which have been isolated from sphingan-producing Sphingomonas strains. The DNA which is isolated from sphingan-producing bacteria is first cloned and then reinserted into sphingan-producing Sphingomonas strains or nonmucoid mutants derived from sphingan-producing strains.

The present invention also comprises an engineered Sphingomonas bacteria into which the above-described isolated DNA segments or fragments have been inserted. These engineered bacteria contain multiple copies of isolated DNA segments or fragments according to the present invention. The engineered bacterium according to the present invention are hyperproducers of sphingan.

The DNA fragments according to the present invention may be isolated, recovered and cloned by techniques which are readily available in the art. Thereafter, the DNA is inserted into bacteria of the genus Sphingomonas in multiple copies, generally as extrachromosal or plasmidic DNA. After insertion into the target bacteria, the production of sphingan is determined by fermenting the engineered bacteria under the same conditions as an identical concentration of non-engineered sphingan-producing bacteria of the same strain. Hyperproducers are determined by their increased sphingan production relative to the non-engineered sphingan-producing strain. DNA sequences for enhancing the production of sphingan polysaccharide from virtually any member of sphingan-producing Sphingomonas sp. bacteria may be readily determined using this procedure.

BRIEF DESCRIPTION OF THE DRAWINGS

FIG. 4 is a diagrammatic representation of the DNA sequence corresponding to the spsB gene, containing approximately 1950 base pairs, of Sphingomonas strain S88, (SEQ ID NO.: 2)

FIG. 5 is a diagrammatic representation of a deduced amino acid sequence of the SpsB protein of Sphingomonas strain S-88, (SEQ ID NO.: 1).

FIG. 6 is a diagrammatic representation of the chemical structures of a number of sphingan polysaccharides representative of those produced by the present invention.

DETAILED DESCRIPTION OF THE INVENTION

Figure 1:
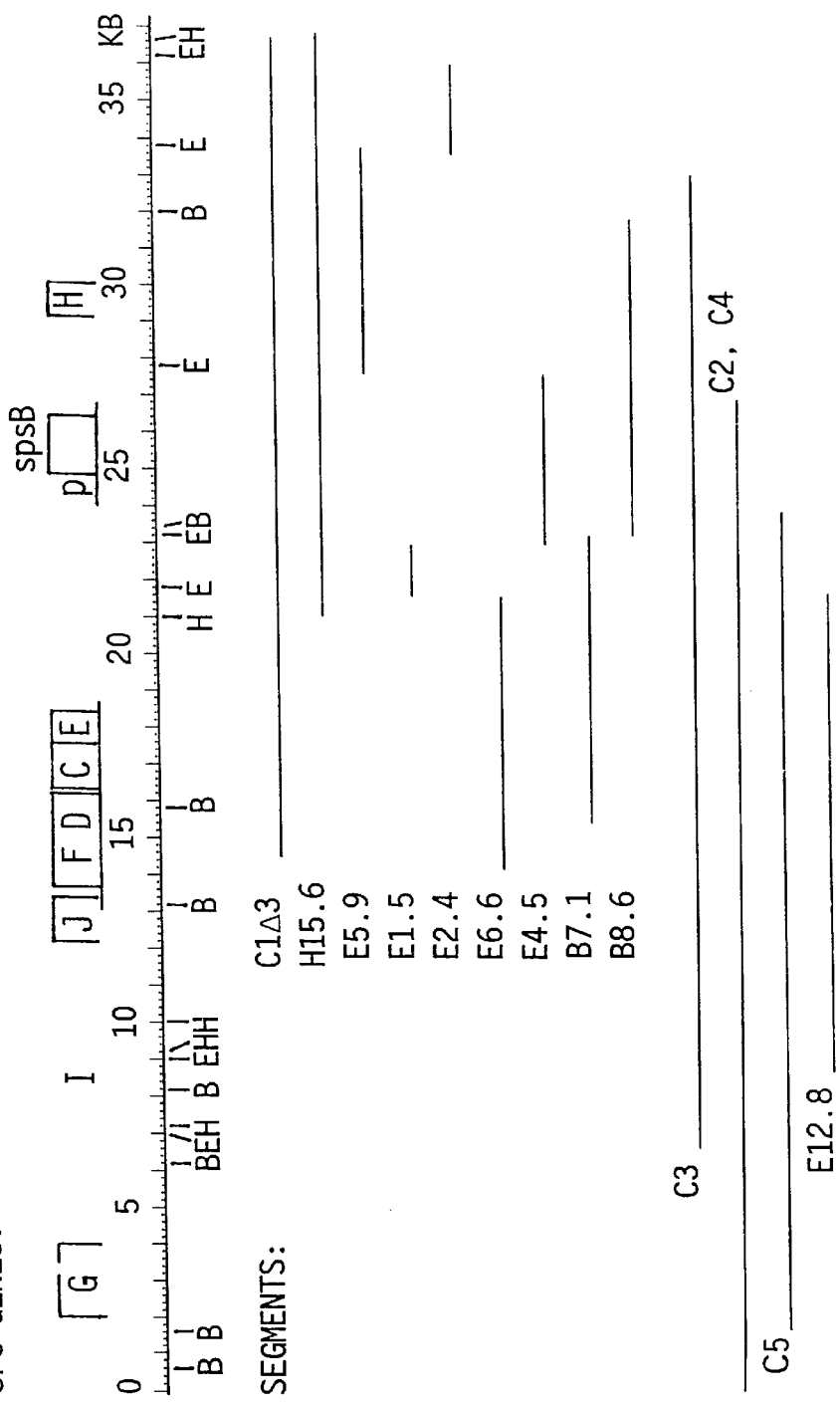
FIG. 1 is a diagrammatic representation of the restriction enzyme cleavage sites of a 37 kilobase nucleotide unit DNA segment isolated from chromosomal DNA of Sphingomonas strain S88 (ATCC accession number 31554). A number of the DNA sequences presented in FIG. 1 were inserted into Sphingomonas bacteria and examined for their ability to enhance sphingan production. Restriction sites for several enzymes are also shown in FIG. 1 (as well as FIG. 2 and 3): B (BamHI), Bg (BglII), E (EcoRI), H (HindIII) and S (SalI). The spsB region, set forth in FIG. 1, corresponds to the DNA sequence which codes for the protein SpsB.

The following terms shall be used throughout the specification in connection with the present invention and have the meaning indicated:

1. The term "sphingan" is used throughout the specification to refer to a group of related but distinct exopolysaccharides secreted by members of the genus Sphingomonas (Pollock, *J. Gen. Microbiology* 139:1939–1945, 1993). The structures of the sphingans are all somewhat related. The main chain of each sphingan consists of a related sequence of four sugars—D-glucose, D-glucuronic acid, L-mannose and L-rhamnose. Polysaccharide members of the sphingan group are distinguishable from each other by virtue of the carbohydrates which comprise the polymer backbone (either glucose-glucuronic acid-glucose-rhamnose or glucose-glucuronic acid-glucose-mannose) and the sidechains. The sphingan polysaccharides may contain carbohydrate side chains and acetyl or pyruvyl groups attached to carbohydrates on the polymer backbone. See Mikolajczak, et al., *Appl. and Env. Microbiol.*, 60:402, (1994). The diagrammatic representation of the chemical structures of various sphingans produced using the DNA segments and fragments and general methods according to the present invention are generally set forth in FIG. 6. The structures of sphingans gellan (S-60), welan (S-130), rhamsan (S-194), S-88, NW-11, S-198 and S-657 are generally set forth in FIG. 6.

Typically, members of the sphingan polysaccharide family may be represented by the following general repeating chemical structure:

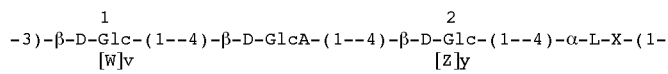

wherein Glc is glucose; GlcA is glucuronic acid; Rha is rhamnose; Man is mannose; X may be Rha or Man; Z is attached to Glc residue number 2 and may be α-L-Rha-(1–6)-α-L-Rha, α-L-Man or α-L-Rha; W is attached to Glc residue number 2 and may be β-D-Glc-(1–6)-α-D-Glc or α-L-Rha, subscripts v and y may be 0, 0.33, 0.5, 0.67 or 1, and wherein the reducing end of the polymer is toward the X residue of the backbone. As used herein, the term "backbone" refers to that portion of the structure which excludes chains W and Z, i.e., when v and y are equal to 0.

Some members of the sphingan polysaccharide family are acetylated at various positions. However, the polysaccharides may be subjected to chemical deacylation in a conventional manner to remove the acyl groups. For example, gellan has the same carbohydrate backbone as welan (i.e., X=Rha), but lacks the side chain sugar (i.e., v=0 and y=0) and the glucose residue 1 is fully substituted with glycerate. The gellan subunit structure is also acylated at unknown positions.

2. The term "Sphingomonas" is used throughout the specification to refer to strains of gram-negative bacteria from the genus Sphingomonas which produce exopolysaccharides or sphingans, as described above. A number of gram-negative bacteria from the genus Sphingomonas may be used in the present invention, either as a source of isolated DNA sequences which may be reinserted into other strains of sphingan-producing bacteria (preferably, gram-negative bacteria from the genus Sphingomonas) to produce sphingan hyperproducers according to the present invention, or as target bacteria for inserting exogenous DNA sequences to produce sphingan hyperproducers.

Sphingan-producing gram-negative bacteria were first identified as belonging to the genus Sphingomonas in 1993. See Pollock, *J. Gen. Microb.*, 139, 1939 (1993). It has yet to be established precisely to which species each strain belongs. The closest species to the sphingan-producing strains of Sphingomonas appears to be *Sphingomonas paucimobilis*. However, it is premature to refer to these strains as belonging to that species until a detailed and finalized taxonomic analysis is available. It is noted that the sphingan-producers of the genus Sphingomonas were initially classified into several different genera.

The currently recognized species of Sphingomonas include *S. paucimobilis, S. parapaucimobilis, S. adhaesiva, S. capsulata*, and *S. yanoikulyae*. See Yabuuchi, et al., *Microbiol. Immunol.*, 34, 99 (1990). Previously, these species of Sphingomonas had been incorrectly assigned to the genus Pseudomonas.

3. The terms "donor" and "recipient" are used to describe, respectively, bacteria from which DNA sequences are taken and into which DNA sequences are inserted or incorporated.

4. The term "strain" or "Sphingomonas strain" is used to describe gram-negative bacteria of the genus Sphingomonas which produce a particular sphingan exopolysaccharide (based upon chemical structure). For simplicity, the sphingan-producing strains of Sphingomonas are referred to by the sphingan polysaccharide produced by that strain. For example, Sphingomonas strain S88 produces sphingan polysaccharide S-88, Sphingomonas strain S60 produces sphingan polysaccharide S-60 (gellan), etc. Sphingomonas strains S88 (ATCC number 31554), S60 (ATCC number 31461), NW11 (ATCC number 53272), S130 (ATCC number 31555), S194 (ATCC number 31691), S198 (ATCC number 31853), S657 (ATCC number 53159) and S7 (ATCC number 21423), among numerous others, are representative of strains which are useful in the present invention.

5. The term "hyperproducer" is used throughout the specification to describe engineered bacteria containing multiple copies of DNA segments or fragments isolated from the same strain or a different strain of sphingan-producing bacteria which produce significantly greater (at least about 5% more on a weight by weight basis) sphingan polysaccharide compared to non-engineered or wild type bacteria of the same strain as the engineered bacteria which are fermented under identical or substantially identical fermentation conditions.

6. The term "isolated" is used to describe DNA which has been removed from a microorganism and subjected to at least some degree of purification, i.e., one or more purification steps. Preferably, isolated DNA is prepared in substantially pure form, i.e., in a form which contains only minor quantities of contaminating material which will not affect the ability of the isolated DNA to be fragmented or segmented by restriction enzymes, cloned into multiple copies or inserted into plasmid vectors or otherwise inserted or incorporated into bacteria.

7. The term "DNA" or "chromosomal DNA" as used throughout the specification with respect to the DNA isolated from Sphingomonas describes DNA which is found in the chromosomes or endogenous plasmids of Sphingomonas sp., generally prior to isolation from the microorganism.

8. The term "sequence" is used to describe a specific segment of is DNA which is either identified by its nucleotide units or by its pattern of sites for restriction enzyme cleavage, generally isolated from DNA of a sphingan-producing bacteria of the genus Sphingomonas using restriction enzymes, the resulting DNA sequence being inserted into a bacteria to produce a hyperproducer or alternatively subjected to further restriction to produce small portions or fragments of DNA smaller than said sequence. The term "portions" or "fragments" is used to describe DNA sequences which are generally smaller than DNA segments.

9. The terms "inserted", "inserting", "incorporated" or "incorporating" are used throughout the specification to describe the process and outcome of transferring DNA segments isolated from the chromosomal DNA of a sphingan-producing Sphingomonas strain into the same or a different recipient sphingan-producing Sphingomonas strain. The outcome is a hyperproducer strain containing at least two copies of at least a substantial part of the transferred DNA segment.

By way of example, isolated DNA may be introduced first into plasmid vectors, for example, pRK311 or pSEB24, among numerous others, by well-known techniques in the art, cloned and then transferred by conjugation into a recipient Sphingomonas bacterium. After insertion into a recipient Sphingomonas bacterium, the plasmid vector containing the relevant DNA fragment will then replicate in the recipient cell to give several (at least two and usually 4–20) copies of the DNA segment necessary for hyperproduction of sphingan polysaccharide. In addition to plasmid vectors, bacteriophage vectors and transposon vectors may also be used.

A number of plasmid vectors are suitable for use to insert isolated DNA segments or fragments into recipient bacteria. In addition to plasmids pRK311 and pSEB24 described above, the following plasmids, among numerous others, are also useful: broad-host-range plasmids of incompatibility group P-1, such as RK2 and derivatives therefrom such as pRK290, pRK293, pRK404 (Ditta, et al., Plasmid, Vol. 13, pp. 149–153) and other derivatives containing the oriT gene from plasmid RP4 which allows plasmid mobilization such as pSUP101 (See Simon, et al., *Bio/technology*, November, 1983) as well as plasmids pLAFR1 and pLAFR3 (Friedman, et al., *Gene*, 18, 289, 1982); and broad-host-range plasmids of incompatibility group Inc-Q, such as RSF1010 and derivatives therefrom such as pMMB22 and pMMB66 (Fürste, et al., *Gene*, 48, 119, 1986).

The use of conjugation to transfer the plasmid vectors into recipient bacteria is generally effective. In other genera of bacteria, it is more common to use transformation of competent cells with purified DNA.

Electroporation has also been used with Sphingomonas to introduce DNA fragments or plasmids into the bacteria. (See, 1992, Monteiro, et al., *J. of App. Bacteriol.*, 72, 423). Using this method, it is possible to incorporate two or more cellular copies of isolated DNA segments or fragments into recipient Sphingomonas bacteria by simply adding isolated DNA to the bacterium and then achieving transfer across the cellular membrane using the electroporation method.

Monteiro, et al., supra, describes electroporation as a means for introducing DNA into Sphingomonas. Electroporation is functionally the same as transformation of chemically treated competent cells, for example, after treatment of cells with calcium chloride or rubidium salts. The DNA to be transformed is purified by standard methods and may or may not be in plasmid form. Transformation, however, usually is most efficient when the DNA is double-stranded and closed circular. Therefore, it is not necessary to use the conjugation method of introducing DNA into Sphingomonas. Nor is it necessary to have the cloned segments inserted into a plasmid, bacteriophage or transposon vector. It is preferred, however, to first introduce isolated DNA into plasmid vectors and then transfer the plasmids containing the isolated DNA fragments into the bacteria.

Maintaining the DNA segments on plasmids or other vectors such as bacteriophage or transposon vectors in the recipient Sphingomonas is not necessary. It is routine to introduce additional copies of a DNA segment into the bacterial DNA so that the segments are replicated each generation by the same mechanism that replicates the bacterial DNA. The following examples section contains two examples which detail procedures for introducing additional copies of DNA into the bacterial DNA so that the segments are replicated each generation by the same mechanism which replicates the bacterial DNA.

10. The term "multiple copies" is used throughout the specification to describe exogenous DNA sequences, fragments or segments (at least substantial parts of said DNA) which are incorporated into Sphingomonas bacteria in at least two and preferably at least four copies. More preferably, the number of copies of a DNA sequence, fragment or segment which is inserted into a bacterium of the genus Sphingomonas, eventually ranges from about four to about 20. It is noted that in certain instances, a DNA sequence may be incorporated into a single plasmid vector, transferred into the Sphingomonas bacteria by conjugation and the plasmid may replicate in the recipient cell to provide two or more copies of the DNA sequence, segment or fragment.

11. The term "biosynthesis" is used throughout the specification to describe the biological production or synthesis of sphingan by Sphingomonas bacteria. Sphingan polysaccharides are synthesized from individual carbohydrate units in a series of steps controlled by a number of enzymes of the bacteria.

12. The term "engineered" is used throughout the specification to describe those recipient Sphingomonas bacteria into which exogenous DNA has been incorporated, preferably as multiple copies. Engineered bacteria according to the present invention are hyperproducers of sphingan polysaccharide.

13. The term "encoding genetic information" is used throughout the specification to describe DNA sequences which contain genetic information in the form of a particular order of nucleotide units. The genetic information in the DNA sequence (of any length) is considered "beneficial or essential" for the biosynthesis of sphingan in Sphingomonas bacteria, if, in multiple copies in an engineered bacteria, it will enhance sphingan production by the engineered bacteria. The term "beneficial or essential" is used to describe DNA which is isolated from Sphingomonas bacteria and codes for genetic information which, when incorporated in multiple copies in a Sphingomonas bacterium, transforms that bacterium into a hyperproducer of sphingan polysaccharide.

14. The term "interstrain complementation" is used to describe the incorporation into a second strain of Sphingomonas of DNA sequences, segments or fragments which are isolated from a first and different strain of Sphingomonas. An unexpected aspect of the present invention is the discovery that DNA fragments from different strains of Sphingomonas may be incorporated as multiple copies into other strains of Sphingomonas to produce hyperproducers of sphingan polysaccharide. The DNA fragments useful in the present invention also exhibit intergeneric complementation (e.g. to enhance xanthan production in *Xanthomonas campestris*).

The present invention relates to the discovery that DNA sequences obtained from donor sphingan-producing Sphingomonas bacteria and incorporated as multiple copies into the same strain or a different strain of recipient Sphingomonas bacteria will transform the recipient Sphingomonas bacteria into a hyperproducer of sphingan polysaccharide. It further has been discovered that even where the DNA sequence is isolated from bacteria which produce one type of sphingan polysaccharide, that sequence may be incorporated as multiple copies into a different strain of Sphingomonas bacteria and produce a hyperproducer of that different strain without contamination of sphingan polysaccharide characteristic of the donor bacteria.

The relevant DNA sequence which is incorporated into the recipient bacteria encodes genetic information which is beneficial or essential for the biosynthesis of sphingan polysaccharide. For example, the beneficial or essential genetic information may be responsible for or involved in the biosynthesis of sphingan by the bacteria in any number of ways. The exogenous DNA may have a beneficial effect on the biosynthesis of sphingan for example, by expressing the synthesis of enzymes or other proteins involved in a rate-limiting enzymatic step, by inducing the synthesis of an enzyme, cofactor or other biochemical component which results in the increased production of polysaccharide, by binding to one or more repressor genes and preventing the expression of a repressor which normally inhibits the production of rate limiting steps in the biosynthesis of the polysaccharide.

The relevant DNA sequences are isolated from strains of Sphingomonas using techniques and methods which are standard in the art. The bacteria are generally cultured (standard fermentation procedures with glucose concentration below about 0.5%, preferably about 0.1% to about 0.2%, as described in further detail hereinbelow) to produce a broth containing high concentrations of bacteria. The bacterial cells are then centrifuged and resuspended for DNA extraction. The DNA may be extracted from the bacteria by first removing the proteins from the mixture, and then precipitating the high molecular weight DNA with ethanol or isopropanol. See Birnboim and Doly, *Nucl. Acids Res.*, 7, 1513 (1979).

After precipitation as described above, the isolated DNA segments or fragments generally are cloned to produce DNA for insertion into recipient Sphingomonras. By way of example, the high molecular weight DNA sequences from above are partially digested with a restriction enzyme (for example, SalI enzyme) and electrophoresed using standard methods. See Loftus, et al., *BioTechniques*, 12, 172 (1992). After electrophoresis, the larger DNA fragments (20 kbp and larger) are further purified (extraction and precipitation).

The DNA fragments isolated from the bacteria are thereafter inserted directly into cloning vectors (generally, plasmids) for cloning the DNA or alternatively, are further subjected to restriction enzymes to produce smaller DNA fragments which are inserted into cloning vectors. The cloning of DNA in the present invention relies on general techniques and methods which have become standard in the art. It is noted that any number of methods may be used to clone the DNA segments according to the present invention and the present invention is not limited, for example, to the use of plasmidic cloning vectors. For example, the DNA fragments may be cloned by insertion into a bacteriophage vector, such as, charon 4A, EMBL3 (See Rodriguez and Denhardt, Vectors, Chapter 2, pg. 43, 1988, Butterworth Publishers, Boston) or P1 (1990, Sternberg, *Proc. Natl. Acad. Sci.* U.S.A., 87, 103–107)

As described in detail in example 1, below, the DNA fragments first are prepared for insertion into a cloning vector. Any number of cloning vectors for producing DNA segments or fragments according to the present invention may be used. In the present invention, however, it has been found advantageous to clone the DNA segments or fragments in the same plasmid vector which will be used for inserting exogenous DNA into a recipient bacteria by conjugation. It is possible, however, to utilize a cloning vector (plasmidic or other) which is not going to be used as a vector for inserting the DNA into a recipient bacteria, especially where a transformation process is going to be used to insert the DNA into the recipient bacterium.

After insertion into a cloning vector, the vector containing the isolated DNA is packaged into a bacteriophage, transferred to a bacterium (generally, *E. coli*) by a transfection process, and replicated within the transfected bacteria. The resulting colonies of bacterial cells containing cloned DNA are pooled and stored or utilized directly.

The cloned DNA is thereafter screened to determine the relative efficacy of a DNA fragment to enhance the production of sphingan in Sphingomonas. In the screening method, the DNA in an appropriate vector is then inserted into a recipient strain of Sphingomonas by conjugation (for example, tri-parental mating, as described by Ditta, et al., *Proc. Natl. Acad. Sci.* USA, 77, 7347 (1980)), the resultant engineered bacterium containing the DNA in multiple copies and its sphingan production is then tested to determine activity.

The DNA segments or fragments determined to enhance sphingan production are then transferred into a recipient Sphingomonas strain to produce a hyperproducer strain containing at least two copies of at least a substantial part of the transferred DNA segment as previously described.

A preferred screening method has been developed for use in the instant invention. In this method, DNA is screened for the presence of genes beneficial or essential for sphingan synthesis by inserting the DNA in a recipient non-producing strain of Sphingomonas. In this screening method, a non-producing mutant (for example, Sps$^-$ Bac$^r$ of strain S-88) derived from a sphingan-producing strain of Sphingomonas is engineered to contain multiple copies of the DNA to be screened. After growth on nutrient agar plates containing 1–3% glucose of the engineered non-producing mutant and comparison of colonial appearance by the engineered bacteria with non-producing mutant Sphingomonas bacteria which have been grown under identical conditions, a visual determination may be made regarding the ability of that DNA to cause the synthesis of sphingan in Sphingomonas bacteria, in general.

The determination of the ability of a DNA segment or fragment to enhance sphingan producing activity is generally based upon readily recognized phenotypic differences which exist between sphingan-producing bacteria and non-sphingan-producing mutants on culture plates. For example, sphingan-producing Sphingomonas strains are mucoid producers, which often can result in colony formation which is easily differentiated by simple visual inspection (e.g., upright round colonies surrounded by a bright ring for sphingan producers versus flat rough translucent colonies for non-producers).

In certain instances, as described in more detail in example 2, below, when the phenotypic differences between sphingan-producing bacteria and non-sphingan-producing bacteria in one Sphingomonas strain are not easily or readily recognized, the screening process may be modified to screen for the activity of the relevant DNA in bacteria where the phenotypic differences between producers and non-producers are more readily recognized by visual inspection. This aspect of the present invention makes use of the fact that DNA fragments useful in the present invention exhibit interstrain and intergeneric complementation and in multi-copies will enhance sphingan production in virtually all Sphingomonas strains.

DNA segments or fragments useful in the present invention will also exhibit activity in *Xanthomonas campestris*. Consequently, DNA fragments which are not easily screened by using one or more strains of Sphingomonas bacteria may be incorporated into a non-xanthan producing mutant of *X campestris*, for example X59m31, among others, in multiple copies and then screened by visual inspection for the production of xanthan. The non-producing mutants of *X. campestris*, such as X59m31, are readily obtained by selecting survivors of exposure to bacitracin and observing whether the colonies formed by the bacitracin-resistant mutants on YM agar plates are mucoid (producers) or non-mucoid (non-producers) in appearance. (See, Pollock, et al., 1994, *J. Bacteriol.*, 176, pp. 6229–6237 and U.S. Pat. No. 5,338,841). Those DNA which exhibit increased production of polysaccharide (sphingan or xanthan) in the screened bacteria, will evidence interstrain or intergeneric complementation and enhance sphingan polysaccharide production in other strains of Sphingomonas bacteria or even different genuses of bacteria (Xanthomonas).

Utilizing the simple screening method in this aspect of the present invention, one of ordinary skill employing readily available cloning and transfer techniques will be able to readily obtain DNA segments or fragments which may be used in the instant invention for enhancing the production of sphingan polysaccharides in Sphingomonas bacteria without engaging in excessive or undue experimentation.

Another aspect according to the present invention relates to the enhanced production of sphingan polysaccharide. To produce sphingan polysaccharide, engineered bacteria according to the present invention are cultured under suitable fermentation conditions, which are well known in the art. A suitable medium or fermentation broth for culturing the engineered Sphingomonas bacteria is an aqueous medium which generally contains a source of carbon such as, for example, carbohydrates including glucose, lactose, sucrose, maltose or maltodextrins, a nitrogen source such as, for example, inorganic ammonium, inorganic nitrate, organic amino acids or proteinaceous materials such as hydrolyzed yeast, soy flour or casein, distiller's solubles or corn steep liquor, inorganic salts and vitamins. A wide variety of fermentation media will support the production of sphingans according to the present invention.

The carbohydrates are included in the fermentation broth in varying amounts but usually between about 1% and 5% by weight of the fermentation medium. The carbohydrates may be added all at once prior to fermentation or alternatively, during fermentation. The amount of nitrogen may range from about 0.01% to about 0.4% by weight of the aqueous medium. A single carbon source or nitrogen source may be used, as well as mixtures of these sources.

Among the inorganic salts which find use in fermenting Sphingomonas bacteria are salts which contain sodium, potassium, ammonium, nitrate, calcium, phosphate, sulfate, chloride, carbonate and similar ions. Trace metals such as magnesium, manganese, cobalt, iron, zinc, copper, molybdenum, iodide and borate may also be advantageously included. Vitamins such as biotin, folate, lipoate, niacinamide, pantothenate, pyridoxine, riboflavin, thiamin and vitamin $B_{12}$ and mixtures thereof may also be advantageously employed.

The fermentation is carried out at temperatures between about 25° and 35° C., with optimum productivity obtained within a temperature range of about 28° and 32° C. The inoculum is prepared by standard methods of volume scale-up, including shake flask cultures and small-scale submerged stirred fermentation. The medium for preparing the inoculum can be the same as the production medium or can be any one of several standard media well-known in the art, such as Luria broth or YM medium. The concentration of carbohydrate can be reduced in the seed cultures to less than about 1% by weight. More than one seed stage may be used to obtain the desired volume for inoculation. Typical inoculation volumes range from about 0.5% to about 10% of the total final fermentation volume.

The fermentation vessel typically contains an agitator to stir the contents. The vessel also may have automatic pH and foaming controls. The production medium is added to the vessel and sterilized in place by heating. Alternatively, the carbohydrate or carbon source may be sterilized separately before addition. A previously grown seed culture is added to the cooled medium (generally, at the fermentation temperature of about 28° to about 32° C.) and the stirred culture is fermented for about 48 to about 96 hours, producing a high viscosity broth. The sphingan polysaccharide is recoved from the broth by the standard method of precipitation with an alcohol, generally isopropanol.

By way of specific example, this application discloses DNA segments or fragments which were isolated from several bacterial strains, in particular, Sphingomonas strains S88, S60 and NW11 (available from the American Type Culture Collection as deposits ATCC31554, ATCC31461 and ATCC 53272, respectively). These DNA segments or fragments were found to be useful for increasing sphingan S-88, S-60 and NW-11 production in the respective strains of Sphingomonas bacteria when they were incorporated in multiple copies as extrachromosomal (plasmid) DNA in the strains of bacteria.

In the case of Sphingomonas strain S88, the isolated segment of chromosomal DNA is approximately 37 kbase units in size, contains at least 8 genes and is believed to contain as many as 20 genes. As shown by the map of clones for S88 in FIG. 1, the 37 kbp region is the combined extents of two clones: c1Δ3 and c2. A number of DNA sequences from this 37 kbase DNA sequence labelled c1Δ3, C2, C3, C4, C5, H15.6, B7.1, B8.6, E5.9, E1.5, E2.4, E4.5, E6.6, E12.8, etc. are also presented in FIG. 1.

Figure 2:
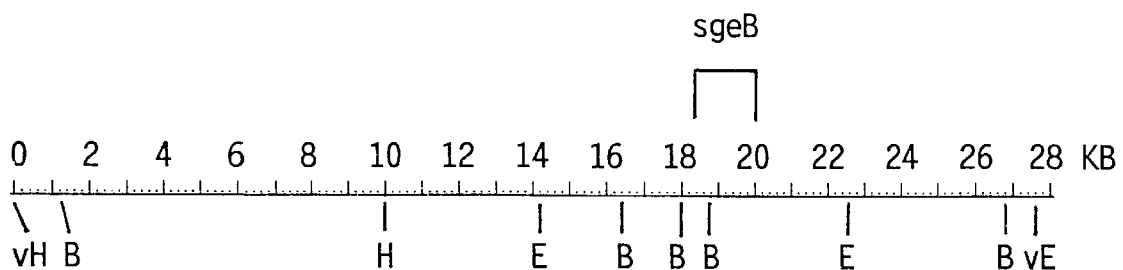
FIG. 2 is a diagrammatic representation of restriction enzyme cleavage sites of a DNA segment (approximately 28 kbase units) isolated from chromosomal DNA of Sphingomonas strain S60 (ATCC accession number 31461). Restriction sites for this DNA sequence are shown in FIG. 2 as B, E and H sites. The sgeB region corresponds to the DNA sequence which codes for the protein SgeB.

In the case of Sphingomonas strain S60, a number of DNA sequences from the chromosomal DNA were isolated including C1, C2 and C3 (see FIG. 2). Sequence C2 was cloned, placed into a pRK311 vector and inserted into Sphingomonas bacteria strains S88, S60 and NW11 to assess sphingan-producing activity (see example 9, described in further detail herein).

Figure 3:
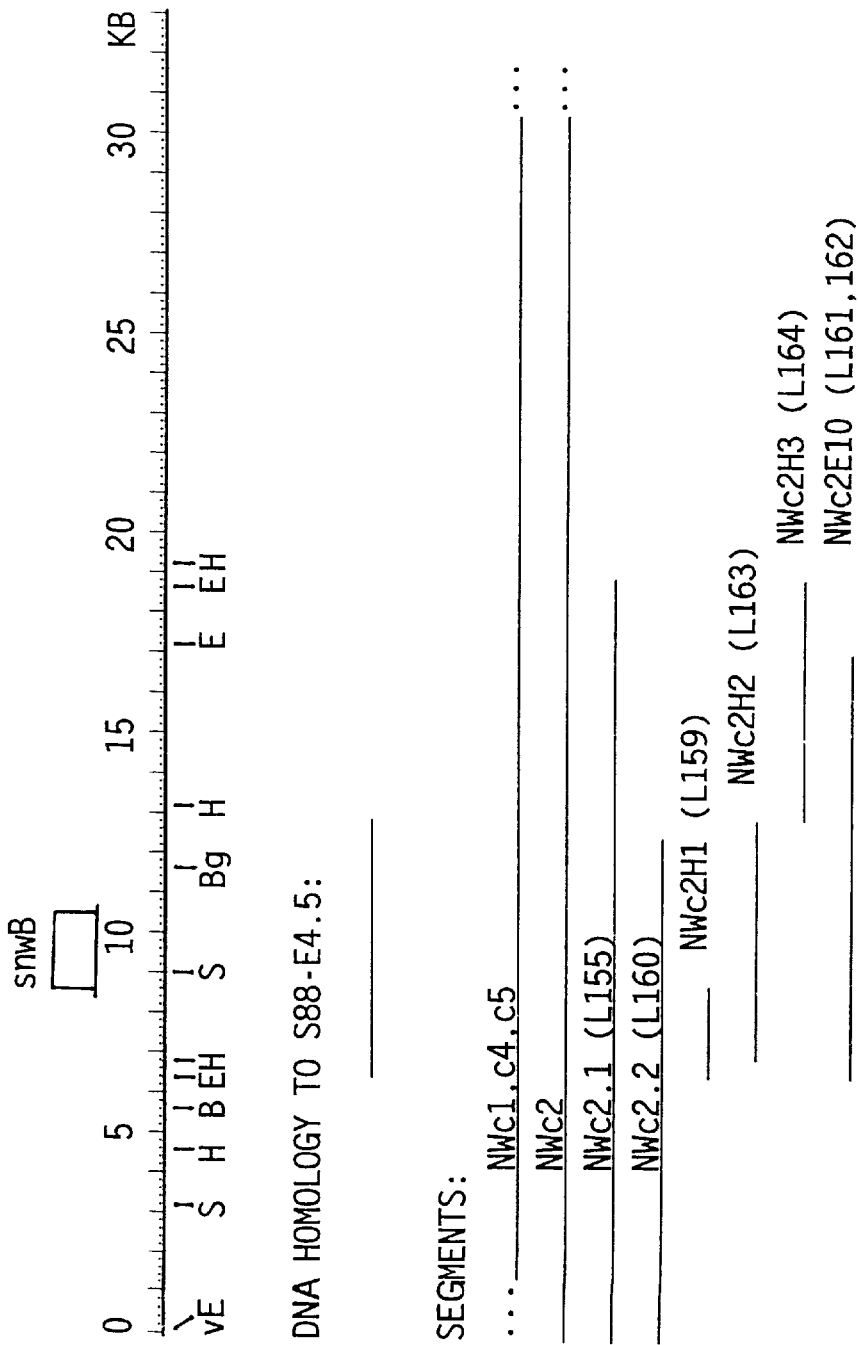
FIG. 3 is a diagrammatic representation of restriction enzyme sites of a DNA segment (approximately 33 kbase units) isolated from chromosomal DNA of Sphingomonas strain NW11 (ATCC accession number 53272). Restriction sites for this DNA sequence are shown in FIG. 3 as E, H, B, Bg and S sites. The snwB region corresponds to the DNA sequence which codes for the protein SnwB.

In the case of Sphingomonas strain NW 11, DNA fragments c1, c2, c2, c2.1, c2.2, c2Hd, c2H1, c2H2, c2H3, c2E10 were isolated (see FIG. 3). Sequence c2.2 was cloned, placed into a pRK311 vector and and inserted into Sphingomonas bacteria strains S88, S60 and NW11 to assess sphingan-producing activity (see example 9, described in further detail herein).

The following DNA segments were prepared using a procedure as generally described above from S88, S60 and NW11 strains of Sphingomonas. Each of these DNA segments (as indicated as full length DNA segments in plasmid vectors), when inserted into one or more strains of Sphingomonas (wild type sphingan producer or nonmucoid mutant derived from wild type producer), changes the bacteria into hyperproducers of sphingan polysaccharide. Each of the DNA segments or fragments is derived from the DNA segment or fragment isolated from Sphingomonas strains, inserted into plasmid vectors as indicated. The DNA segments or fragments are defmed by maps of restriction enzyme cleavage sites (see FIGS. 1, 2 and 3).

Strain S88
- pRK311-S88c1Δ3
- pRK311-S88c2
- pRK311-S88c3
- pRK311-S88c4
- pRK311-S88c5
- pRK311-S88H15.6
- pRK311-S88B8.6
- pRK31 1-S88B7.1
- pSEB24-S88E6.6 train S60
- pRK311-S60c2 strain NW11
- pRK311-NW11c2.2

The cloned DNA can be introduced into wild-type sphingan-producing Sphingomonas or non-sphingan-producing mutants to realize the hyperproduction effect. For example, the cloned DNA in multiple copies may be introduced into either sphingan-producing wild-type strains or nonmucoid mutants derived from sphingan-producing strains, respectively. The resulting engineered bacteria are hyperproducers of sphingan in comparison to sphingan-producing wild-type bacteria or mutant non-producing bacteria of the same strain.

The introduction of multiple copies of the relevant screened DNA into these strains of Sphingomonas bacteria quite unexpectedly and generally increased the sphingan produced by the recombinant bacteria compared to the level of sphingan produced by the wild-type bacteria. The phenomenon was general and the increase in sphingan exhibited interstrain complementation.

In the present invention, after introduction of the cloned DNA into the bacterium in multiple copies, the recombinant bacteria now have sphingan polysaccharide synthesis activity at levels which are elevated relative to the wild type. The DNA segments useful in the present invention carry genes which are beneficial or essential for synthesis of sphingan by Sphingomonas strains, including a DNA fragment which codes for a protein that is required to attach an initial glucose residue onto a carrier isoprenylphosphate, which is an early step in assembling or biosynthesizing sphingan in these strains.

The DNA sequence of the spsB gene (FIG. 4) and the deduced amino acid sequence of the SpsB protein (FIG. 5) are also disclosed. All DNA fragments which contain DNA coding for the SpsB protein (or an analogous protein such as SgeB or SnwB, among others, depending on Sphingomonas strain) may be incorporated into Sphingomonas strains as multiple copies to enhance the production of sphingan by the resultant engineered bacteria.

Likewise, the same is true for DNA segments or fragments containing the sgeB gene (encoding the SpsB-analogous SgeB protein) isolated from S60 Sphingomonas and the snwB gene isolated from NW11 Sphingomonas. The sgeB gene (FIG. 2) is analogous to the spsB gene of the S88 chromosomal DNA in that it is believed (based upon DNA hybridization with fragments corresponding to the spsB gene of S88) to encode a protein which is analogous to the protein encoded by the spsB gene. The snwB region, set forth in FIG. 3, corresponds to the DNA sequence which encodes the protein SnwB. The snwB gene is analogous to the spsB gene of the S88 chromosomal DNA and the sgeB gene of the S60 chromosomal DNA. These DNA fragments may be inserted into plasmids as generally described hereinabove to produce multiple copies for enhancing sphingan production in Sphingomonas.

The spsB gene is believed to code for glucosyl-IP transferase in Sphingomonas S88. There is considerable homology evidenced between the deduced amino acid sequences of SpsB protein and putative glycosyl-IP transferases from other genera of bacteria. The strongest evidence that the spsB gene codes for a glucosyl-IP transferase is the similarity of its deduced amino acid sequence to the sequences of other genes generally believed to code for glycosyl-IP transferases. Indeed there is considerable homology for the carboxyl halves of glucosyl and galactosyl-IP transferases. Although the amino terminal regions lack this extensive homology, the SpsB protein is similar to the RfbP protein of *S. enterica* (1991, Jiang, et al., *Mol. Microbiol.*, 5, 695) in that it has multiple hydrophobic stretches which suggest membrane-spanning domains. The hydrophobic domains of SpsB include amino acids 35–59 (+2.2 average hydropathy), 68–86 (+1.7), 105–123 (+2.3) and 282–303 (+2.9). The position of the latter hydrophobic region is common to these related gene products. It is located adjacent to the region of greatest homology.

In preferred embodiments according to the present invention, DNA segments or fragments containing DNA sequences encoding for glycosyl-IP transferases of various strains of Sphingomonas bacteria, including S88, S60, NW11, S130, S194, S198, S657 and S7, among numerous others, are advantageously employed in multiple copies in recipient Sphingomonas bacteria to enhance sphingan production in the recipient bacteria.

The following examples are provided to illustrate the present invention. The description of the examples should not be misconstrued to limit the scope of the present invention in any way.

EXAMPLE 1

Construction of a Library of DNA Segments from Sphingomonas

DNA fragments essential for synthesis of sphingans were cloned from strains of Sphingomonas. A complete library of DNA segments was prepared as follows. A bacterial strain (S88 in this example) was shaken overnight in 25 ml of liquid YM medium at 30° C. to give a viscous broth containing rafts of cells. YM medium contained 3 g Bacto yeast extract, 3 g Bacto malt extract, 5 g Bacto peptone (Difco) and 10 g D-glucose (Difco) per liter of water. Sodium azide was added to 0.01% and sphinganase enzyme (1994, Mikolajczak, et al., *Appl. Environ. Mirobiol.*, 60, 402) was added for 8 hr at 37° C. to digest sphingan exopolysaccharides to partially reduce the viscosity and rafting of cells. The cells were centrifuged and resuspended for DNA extraction by the method of Bimboim and Doly, *Nucl. Acids Res.*, 7, 1513 (1979). Proteins were removed from the cleared lysate with an equal volume of phenol:CHCl3:isoamylalcohol (24:24:1) by gentle rocking for 16 hr at 25° C. and then with one volume of CHCl3:isoamyl alcohol (24:1) for 3 hr at 25° C. One-tenth volume of 3 M sodium acetate (pH 5.2) was added and the high molecular weight DNA was precipitated with two volumes of ethanol, and then dried and resuspended in 0.5 ml TE (10mM Tris-HCl pH 8, 1 mM EDTA).

According to the cosmid cloning strategy of Loftus, Foster and Ross (*BioTechniques,*, 12, 172, 1992), S88 DNA was partially digested with SalI enzyme, electrophoresed through 1% low melting point agarose in Tris-acetate-EDTA buffer, and fragments larger than 20 kbp were purified by phenol extraction and ethanol precipitation. The SalI-digested S88 DNA was treated with Klenow DNA polymerase to add dCMP and dTMP to the cohesive ends, heated for 20 min at 70° C. and then precipitated with ethanol. The vector plasmid pRK311 (1985, Ditta, et al., Plasmid, 13, 149–153) was digested to completion with BamHI enzyme and then heated for 15 min at 65° C. and purified by phenol extraction and ethanol precipitation. The BamHI-digested pRK311 DNA was treated with Kilenow DNA polymerase to add dGMP and dAMP and then purified as above. The ligation reaction with T4 DNA ligase contained equal molar amounts of vector and insert fragments. All restriction enzymes, Klenow DNA polymerase and T4 DNA ligase were from Stratagene and the manufacturer's reaction conditions were used. After packaging into bacteriophage (Gigapack™ IIXL of Stratagene) the ligated molecules were transferred into *E. coli* DH5α™ by transfection and cells were spread onto LB plates containing tetracycline at a concentration of from 4 to 12 μg/ml. One library of 1700 and one of 3400 Tetr colonies were separately pooled and frozen. The Tetr colonies (10 of 10 tested) contained inserts of 25 to 30 kbp with internal SalI restriction sites.

Similarly, libraries of chromosomal DNA segments were also prepared from other strains of Sphingomonas, including NW11 and S60.

EXAMPLE 2

Isolation of Biosynthetic DNA Fragments for Sphingan S-88

Fragments of DNA cloned in plasmids were screened for the presence of genes essential for sphingan S-88 synthesis by observing restoration of sphingan synthesis in sphingan-negative mutants. Previously, we found that most of the spontaneous bacitracin-resistant mutants of Sphingomonas strain S88 capable of growing on YM plates containing bacitracin at 500–800 μg/ml failed to produce sphingan polysaccharides (Pollock, et al., 1994, J. Bacteriol., 176, pp. 6229–6237). This formed the basis for a simple screening procedure for this special class of mutants.

Mutant S88m260 is a representative member of this Sps⁻ Bac$^r$ group. The failure to make exopolysacclarides by S88m260 and the other Bac$^r$ Sps⁻ mutants resulted in a colony appearace that was more flat, rough-surfaced and translucent compared to the wild type colonies, and the Bac$^r$ Sps⁻ colonies were also surrounded by a narrow light-refracting halo when held up to light and viewed from below. These phenotypic differences were not as obvious as the copious mucoidy of wild type *X. campestris* and flat appearance of corresponding Gum⁻ mutants. The colonial phenotypes were verified by growing cultures in liquid YM medium and weighing the dried exopolysaccharides after precipitation with isopropyl alcohol. Several Sps⁻ mutants were sensitive to bacitracin and subsequently were found to define genes that were essential for sphingan synthesis but that were distinct from the gene associated with the bacitracin-resistant phenotype.

Plasmid DNA from the gene library was transferred from *E. coli* to Xanthomonas or Sphingomonas by tri-parental mating (Ditta et al. *Proc. Natl. Acad. Sci.* USA, 77, 7347, 1980). Mixtures of donor cells containing Mob⁺ Tra⁻ recombinant plasmids (pRK311 with S88 insert), helper cells containing Mob⁺ Tra⁺ pRK2013 plasmid, and exopolysaccharide-negative recipient cells in the ratio of 5:2:10 were spotted onto nonselective YM plates lacking glucose and incubated for 6–16 h at 30° C. Exconjugants were isolated by spreading a loopful of the mating mixture onto plates containing rifampicin (50 μg/ml) to select against the helper and donor cells, and tetracycline (4–12 μg/ml) for pRK311 or chloramphenicol (20 μg/ml) for pSEB24 to select for the recombinant plasmid. To assess complementation the exconjugants of strain S88 were judged by eye as either Sps⁺ (upright round opaque colonies, surrounded by a bright ring when held up to a light and viewed from below) or Sps⁻ (flat rough translucent colonies with no ring).

Attempts to identify the S88 clones directly in nonmucoid mutants of S88 were unsuccessful (none clearly evidenced mucoidy phenotype). We then switched our approach to try to find the clones after transferring the library into nonmucoid mutants of the gumD gene of *X. campestris*. This allowed us to find the initial clone "S88c1" as described in more detail below.

The S88 gene library was mated from *E. coli* into *X. campestris* strain X59m31 which has a Bac$^r$ Gum⁻ defect in the gumD gene (Pollock, et al. *J. Bacteriol.*, 176, pp. 6229–6237, 1994; Thorne et al., *J. Bacteriol.*, 169, 3593, 1987). From this intergeneric mating we found some Gum⁺ Tet$^r$ colonies on YM plates and they appeared at a frequency of about $10^{-3}$ to $10^{-4}$. Individual plasmids were purified from the complemented mutants and transferred back into *E. coli* for restriction analysis. The purified plasmids were mated into Sphingomonas S88m260 and about 10% of the transconjugants became Sps⁺. One plasmid (pRK311-S88c1) was recovered and used for subsequent work. Plasmid pRK311-S88c1 also complemented several additional independently isolated Bac$^r$ Sps⁻ mutations in Sphingomonas strain S88 and Bac$^r$ Gum⁻ mutants of *X. campestris*. We isolated the exopolysaccharides that were secreted into the culture medium by the exconjugants for each intergeneric mating and verified by thin layer chromatography that acid hydrolysates contained the sugar residues expected for the polysaccharide of the recipient cell. Plasmid pRK311-S88c1 restored sphingan synthesis to Sphingomonas and xanthan gum synthesis to *X. campestris*. These results indicated that plasmid pRK311-S88c1 coded for exopolysaccharide biosynthetic functions missing in the Bac$^r$ polysaccharide-negative mutants, and that genes from one genus could replace the missing function in a second genus. The segment S88c1 is similar to segment S88c1Δ3 shown in FIG. 1, except that S88c1 also includes an additional 7.5 kbp HindIII fragment at the rightmost end of S88c1Δ3. The 7.5 kbp segment was specifically deleted from S88c1 to produce the derivative S88c1Δ3.

The above-described method for determining DNA fragments useful for restoring gum production (sphingan gum in Sphingomonas sp. or xanthan gum in *X. campestris*) is reproducible, and additional clones were isolated in independent trials. Screening of the clone library for segments that complemented Sps⁻ Bac$^s$ mutations 76 and 78 of Sphingomonas yielded three additional clones that partially overlapped with S88c1. The three cloned segments were each about 23–27 kb in length. Two of the three segments complemented mutant S88m260. A map of restriction enzyme cleavage sites is given in FIG. 1.

The above-described method is utilized for determining DNA fragments isolated from Sphingomonas strains S60, NW11 and other sphingan-producing Sphingomonas strains which are useful for increasing sphingan production in each of these strains.

EXAMPLE 3

DNA Sequence of the spsB Gene and Deduced Amino Acid Sequence of the SpsB Protein The double-stranded nucleotide sequence for 1950 bp of the spsB region was obtained from a fragment of 3300 bp subcloned from plasmid pSEB24-S88E4.5::Tn#72. The sequence of the coding strand is given in FIG. 4. There was one long open reading frame (ORF) which we named spsB. The coding region began with ATG at nucleotide 361 (base A numbering from the left edge of the S88 DNA shown in FIG. 1) and continued until the TGA stop codon at 1771. This ORF coded for 470 amino acids and was preceded by a putative ribosome binding site. The deduced amino acid sequence using standard single-letter abbreviations is given in FIG. 5. Each letter in the figure corresponds to an amino acid using standard single-letter abbreviations.

EXAMPLE 4

DNA—DNA Hybridization of the Cloned S88 Segment and the Chromosomal DNA of either S88 or S60

To show that the cloned DNA in plasmid pRK311-S88c1Δ3 derived from contiguous sequences of S88 DNA we labeled plasmid S88c1Δ3 DNA and hybridized it to separated restriction fragments of DNA from Sphingomonas strains S88, mutant S88m260, and S60, the wild type producer of gellan. The presence of hybridization to EcoRI fragments of about 1.5, 2.4, 4.5, 5.9, and 12 kbp is consistent with continuity for the cloned DNA in both the wild type and mutant DNA. The leftmost 6.6 kbp fragment shown for S88c1Δ3 is actually 12.3 kbp when the overlapping clones S88c2, S88c3, and S88c4 are digested with EcoRI, because one of the EcoRI sites is from the multiple cloning site of the vector. The hybridization between S88 DNA and S60 DNA, which produces gellan, indicated that similar gene sequences are present but that the gene organization may be different. Because of the structural similarity between the exopolysaccharides secreted by these two Sphingomonas strains we suspect that they have similar transferase genes. The region of S88-S60 homology is given in FIG. 2. In independent tests for DNA homology we localized the homologous region for strain NW11 and S88 as shown in FIG. 3.

EXAMPLE 5

Cloning of the Sphingan Biosynthetic Gene Cluster From Strains S60 and NW11

DNA fragments were isolated from Sphingomonas S60 and NW11. The method was the same as described in the above examples for strain S88. The maps of restriction sites of the DNA fragments from strain S60 and NW11 are provided in FIGS. 2 and 3, respectively.

EXAMPLE 6

Construction of Plasmid pSEB24

Figure 7:
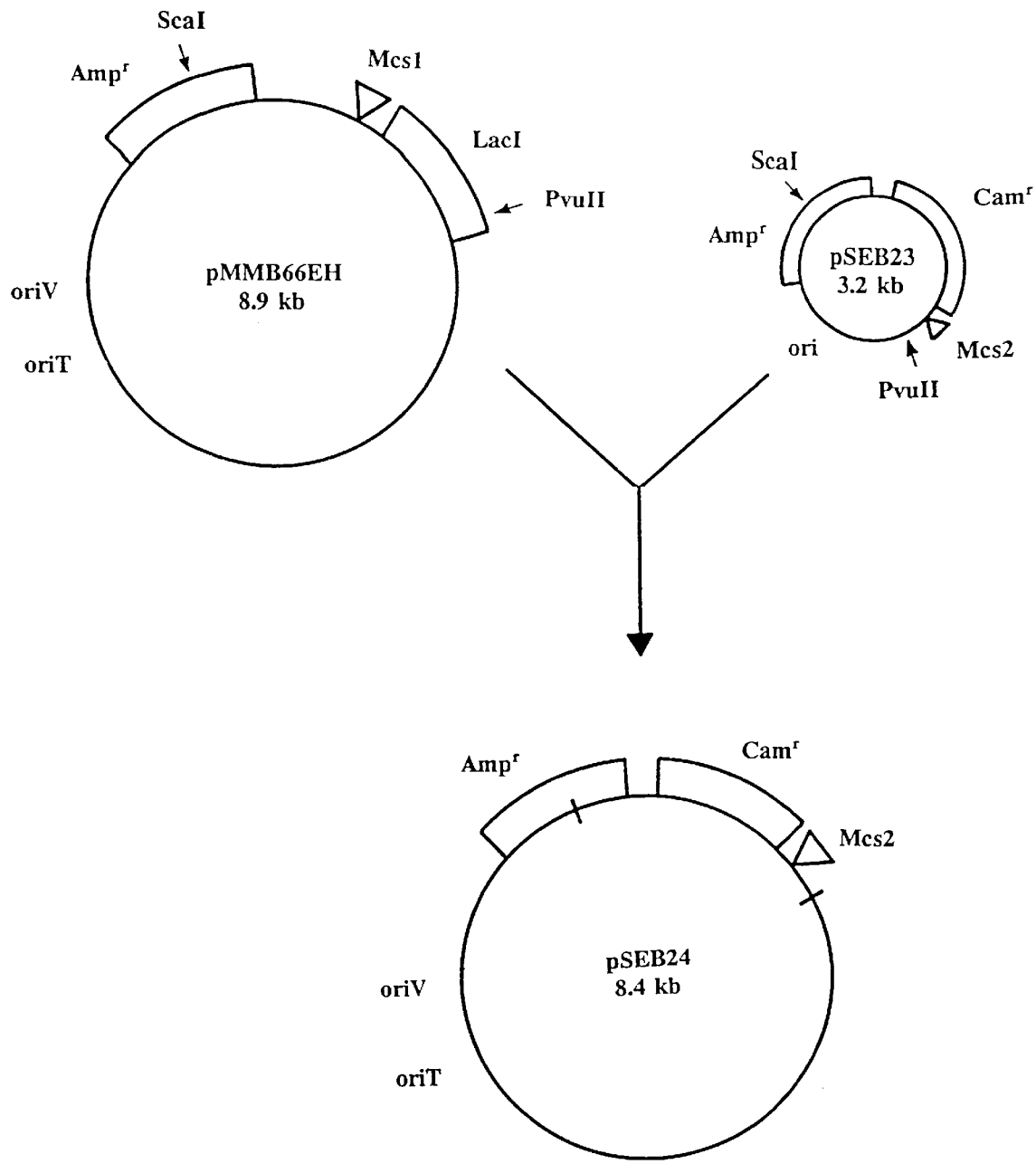
FIG. 7 is a map of the construction of plasmid pSEB24 as detailed in Example 6 of the present application.

Fragments of original clone S88c1 were inserted into the broad host range matable plasmid pSEB24 as diagrammed in FIG. 7. This plasmid was assembled to contain specific replication and mating functions, drug-resistance genes suitable to Sphingomonas and compatible with mini-Tn10kan, and with multiple cloning sites containing many unique restriction sites. First the $Cam^r$ gene on an HpaII-Sau3A fragment of 1031 bp taken from plasmid pC194 of *Staphylococcus aureus* (1982, Horinouchi and Weisblum, *J. Bacteriol.* 150, 815) was made blunt-ended and then ligated to the blunt-ended XbaI site of plasmid pUC13 (1982, Vieira and Messing, *Gene*, 259). The Camr cassette was removed from this plasmid on a BamHI-SalI fragment, blunt-ended, and inserted into pUC12 between the unique SspI site and the nearest of the two PvuII sites (also blunt-ended) to give plasmid pSEB23 which is $Amp^r$ and $Cam^r$ and makes blue colonies with added X-Gal and IPTG. To construct pSEB24, we ligated the ScaI-PvuII fragment of about 2130 bp from pSEB23 to the ScaI-PvuII portion of pMMB66EH (1986, F ürste, et al., *Gene*, 48, 119) to retain oriV (broad host range origin of replication from RSF1010) and to regenerate the $Amp^r$ gene.

EXAMPLE 7

Increased Production of Polysaccharide S-88 after Introduction of Copies of S88 DNA Fragments into Strain S88

Specific restriction fragments of the DNA segment shown in FIG. 1 isolated from strain S88 were inserted by DNA ligation into multicopy plasmid vectors and transferred into wild type strain S88 and progeny nonmucoid mutants of S88 by the triparental conjugation system described in Example 2, above. The polysaccharide synthesis is restored by the cloned DNA when it is transferred into the mutants. The amounts of sphingan exopolysaccharides accumulated by the recombinant plasmid-containing strains and strains lacking the additional plasmid genes were measured after culturing the bacteria in liquid medium. After 24 hour growth at 30° C. with shaking in baffled flasks, two volumes of isopropyl alcohol were added to precipitate the exopolysaccharides. Two to three independent cultures were tested for each strain. The precipitates were collected on filters, dried at 80° C. and weighed. The average weight of precipitate and the standard deviation are given for each strain below in Table 1. The recombinant strains carrying additional copies of the cloned genes produced more sphingan S-88 than wild type strains carrying only the normal set of biosynthetic genes.

TABLE 1

| | Isopropyl alcohol precipitate | |
|---|---|---|
| Host | Plasmid | Dry weight (mg) and standard deviation | Relative weight |
| S88 | None | 105 ± 9 | 1.0 |
| S88m265 | pRK311-S88c1Δ3 | 148 ± 16 | 1.4 |
| S88m265 | pRK311-S88c2 | 175 ± 16 | 1.7 |
| S88m265 | pRK311-S88c3 | 160 ± 7 | 1.5 |
| S88m265 | pRK311-S88c4 | 123 ± 14 | 1.2 |
| S88m265 | pRK311-S88H15.6 | 162 ± 5 | 1.5 |
| S88m265 | pRK311-S88B8.6 | 194 ± 7 | 1.8 |
| S88m265 | pRK311-S88E4.5 | 154 ± 36 | 1.5 |
| S88 | None | 114 ± 12 | 1.0 |
| S88#78 | pRK311-S88c1Δ3 | 171 ± 2 | 1.5 |
| S88#78 | pRK311-S88c2 | 179 ± 7 | 1.6 |
| S88#78 | pRK311-S88c3 | 200 ± 9 | 1.8 |
| S88#78 | pRK311-S88c4 | 189 ± 10 | 1.7 |
| S88#78 | pRK311-S88c5 | 151 ± 4 | 1.3 |
| S88#78 | pSEB24-S88E6.6 | 171 ± 35 | 1.5 |
| S88#78 | pSEB24-S88E12.8 | 114 ± 10 | 1.0 |

It will be obvious to the skilled practitioner that the restriction map and nucleotide sequence of the spsB gene and surrounding DNA provide sufficient information for the construction by standard recombinant DNA methods of numerous additional sub-fragments of the approximately 37 kb region. And that these additional fragments can be tested by the methods described here to identify segments that also cause a similar increase in production of sphingan polysaccharides. From Table 1, one can see that a small fraction of the sub-segments (for example pSEB24-S88E12.8) show no stimulation of production. Nevertheless, virtually all of the sub-segments cause the increased polysaccharide accumulation. From our testing to date we believe that pSEB24-S88B8.6 and pRK311-S88c3 give the greatest stimulus to sphingan production.

The increased production does not require the presence of antibiotics in the culture to maintain a selection for the recombinant plasmids.

The increased production can result from the insertion into the chromosome or endogenous native plasmids of one or more DNA fragments, preferably encoding a gene or set of genes from this chromosomal segment. One of ordinary skill can readily introduce additional DNA fragments into a sphingan-producing bacterium by inserting DNA fragments containing relevant sphingan-producing genes into the resident bacterial chromosome, into endogenous native plasmids or into exogenous plasmid vectors. It is noteworthy that the results which have been evidenced in this application indicate that increased sphingan production is not dependent on the use of any particular plasmid vector.

Also within the scope of the present invention is the fusion of any of the above-described DNA fragments encoding gene segments or group of genes to DNA sequences known to control gene expression, for example and without limitation, the lac promoter of *Escherichia coli*.

EXAMPLE 8

Identification of Exopolysaccharide Produced By Recombinant S88 Strains as Sphigan S-88

To verify that the exopolysaccharide produced by the engineered strains was the same as the recipient type, we identified the monosaccharides in acid hydrolysates by thin layer chromatography.

Extracellular xanthan from *X. campestris* and sphingan S-88 from Sphingomonas were separated from liquid culture media by precipitation with 2–3 volumes of isopropyl alcohol, dried at 80° C. and weighed. The polysaccharides were resuspended in high performance liquid chromatography (HPLC) water at 5 mg/ml. Anhydrous trifluoroacetic acid (88 μl; from Sigma Chemical Co.) was mixed with 75 μl HPLC water (Baker) and 225 μl polysaccharide (5 mg/ml) in a 0.6 ml microcentrifuge tube and incubated at 95° C. for 16 h. The hydrolysates were dried under vacuum, resuspended in 200 μl HPLC water, placed in a new microcentrifuge tube, dried again and resuspended in 45 μl HPLC water. The samples (25 μg/ml) could be stored frozen. Sugar standards (D-glucose, D-glucuronic acid, D-mannose, L-mannose, L-rhamnose, and L-fucose) were resuspended in HPLC water at 4 mg/ml. Precoated, channelled, silica gel chromatography plates (Kieselgel 60 CF 254, 10 20 cm, E. Merck) were soaked overnight in 0.3 M $NaH_2PO_4$, dried 30 min at room temperature and then 10 min at 95° C. Samples of 1–2 μl were spotted and the chromatogram was exposed to a rising solvent mixture of 40 ml acetone, 5 ml butanol and 5 ml deionized water for 2.5 to 3 h at room temperature. The plate was dried at 65° C. for 3 min and then stained by dipping in a solution of 25 ml acetone, 0.5 ml aniline, 0.5 g diphenylamine and 3.75 ml phosphoric acid, followed by drying for 30 min at 95° C. When *X. campestris* was the recipient of the S88 DNA fragments, glucose, mannose and glucuronic acid were present. When Sphingomonas strain S88 was the recipient for the gumD gene of *X. campestris* then rhamnose, glucose, mannose and glucuronic acid were present in amounts similar to S-88 exopolysaccharide.

EXAMPLE 9

Stimulation of Production of Sphingans S-60, NW-11, and S-130 by DNA Fragments Obtained from Strains S88, S60 and NW11

The DNA fragments obtained from strains S88, S60 and NW11 following the general procedure set forth in example 7, above were used to increase production of the sphingans S-60, gellan (S60) and NW-11 in Sphingomonas strains. The results in are given in the following Table 2.

TABLE 2

| | | Isopropyl alcohol precipitate | |
|---|---|---|---|
| Host | Plasmid | Dry weight (mg) and standard deviation | Relative weight |
| S88 | pRK311 | 98 ± 5 | 1.0 |
| S88 | pRK311-S88c2 | 155 ± 24 | 1.6 |
| S88 | pRK311-S60c2 | 133 ± 11 | 1.4 |
| S88 | pRK311-NWc2.2 | 165 ± 15 | 1.7 |
| S60 | pRK311 | 49 ± 11 | 1.0 |
| S60 | PRK311-S88c2 | 73 ± 2 | 1.5 |
| S60 | PRK311-S60c2 | 74 ± 2 | 1.5 |
| S60 | pRK311-NWc2.2 | 55 ± 6 | 1.1 |
| NW11 | pRK311 | 98 ± 5 | 1.0 |
| NW11 | pRK311-S88c2 | 105 ± 6 | 1.2 |
| NW11 | pRK311-S60c2 | 124 ± 5 | 1.4 |
| NW11 | pRK311-NWc2.2 | 100 ± 1 | 1.2 |

In the general approach, DNA fragments isolated from a particular strain of Sphingomonas may be used to increase production of a sphingan (not produced by that strain) in a different strain of Sphingomonas by inserting the isolated DNA fragments in multiple copies following the techniques and methods set forth in the above examples and in particular, example 7.

In the general approach supported by the instant experiment, a DNA fragment containing genetic material essential for the production of sphingan in any Sphingomonas strain may be inserted into an appropriate plasmid vector or otherwise and introduced in multiple copies into a sphingan-producing or nonmucoid mutant of the same or a different Sphingomonas strain from which the DNA is isolated, which is a sphingan producer or is a non-producing mutant of the sphingan-producing strain. The resulting engineered Sphingomonas microorganism produces sphingan in amounts which generally exceed that produced by the non-engineered, non-mutant sphingan producer under identical fermentation conditions.

The following experiments are presented to show that the incorporation of multiple copies of DNA fragments into strains of Sphinogmonas, as well as other bacteria is routine.

EXAMPLE 10

Insertion of Lactose-Utilization Genes Into the Chromosome of *X. Campestris*

Using standard cloning methods involving restriction enzymes and DNA ligation, we inserted the lactose-utilization genes from a transposon, Tn951, adjacent to a previously cloned segment of *X. campestris* DNA carried on a plasmid that could not replicate in *X. campestris*. Thorne, et al., *J. Indust. Microbiol*., 3, 321 (1988). The recombinant plasmid was then transferred into *X. campestris* by conjugation. In the recipient bacterium, the homologous DNA from *X. campestris* located adjacent to lactose-utilization genes recombined with the cellular DNA by normal homologous recombination causing the lactose-utilization genes to become attached to and contiguous with the bacterial chromosome. The result was the stable insertion of the cloned segment into the bacterial chromosome. This is explained more fully in FIG. 2 of Thorne et al. The same approach to inserting genes into bacteria has been used by others on numerous occasions.

It is noteworthy that it is not necessary to use a plasmid as the vector to introduce exogenous DNA into a bacterium in advance of the DNA recombination described above. DNA segments carried by bacteriophage or by transposons are also well known to insert themselves into the bacterial chromosome by site-specific DNA recombination. Usually, bacteriophages, insert specifically at one or a few locations, whereas transposons usaally insert at numerous essentially random locations. Furthermore, it is not necessary for the DNA to be carried into the cell attached to a cloning vector, such as a plasmid. It is well known that DNA fragments can enter bacterial cells by transformation and retain the ability to recombine with the cellular DNA.

EXAMPLE 11

Site-Specific Insertion of a Gene Coding for Resistance to Kanamycin Into Sphingomonas S88 Bacterial DNA at Several Different Randomly Selected Locations This example demonstrates that it is routine to insert segments of cloned DNA into the cellular DNA of Sphingomonas. First, the S88E12.8 fragment (see FIG. 1) was ligated into the EcoRI site within the multiple-cloning site of the plasmid vector pSEB26. Plasmid pSEB26 has the ampicillin-resistance gene, chloramphenical-resistance gene, multiple-cloning site, Lac segment, and oriT as in plasmid pSEB24 shown in FIG. 7. However, it differs by having a narrow-host-range origin of replication ftom plasmid pBR322 instead of the broad-host-range oriV sequence of plasmid pSEB24. The pBR322 origin allows the plasmid to replicate in *Escherichia coli*, but not in Sphingomonas. Therefore the only way DNA sequences cloned into plasmid pSEB26 can persist in Sphingomonas is if they become integrated into the bacterial DNA, such as the chromosome or endogenous plasmids, before the plasmid is lost from the cell or culture. Second, by routine methods, the pSEB26-S88E12.8 plasmid was exposed to mutagenesis with transposon mini-Tn10kan (1991, Kleckner, et al., 204, pp. 139–180). The result was the insertion of a kanamycin-resistance gene into the plasmid. We isolated several independent insertions of the kanamycin-resistance gene each at a different location within the S88E12.8 segment. Third, using the triparental mating scheme we separately transferred each of the recombinant plasmids into Sphingomonas S88 and selected for kanamycin-resistant progeny. In virualwly every case, the S88 DNA sequences located on either side of the kanamycin-resistance gene recombined with the recipient cell's chromosome such that the kanamycin-resistance gene became integrated into the bacterial chromosome. By integrating into the bacterial chromosome the gene was able to survive the inability of the vector plasmid to replicate in Sphingomonas.

This example shows that exogenous DNA segments (in this case the kanamycin-resistance gene) can be introduced into a recipient bacterium so that the incoming gene becomes integrated into the bacterium chromosome. The location of integration is determined by the DNA sequences that are adjacent to the gene. In this example the exogenous gene integrated into different sites within the E12.8 segment of strain S88. Integration by homologous recombination is a routinely practiced method of gene manipulation.

DEPOSITS

The following have been deposited with the American type Culture Collection located at 12301 Parklawn Drive, Rockville, Md. 20852 pursuant to the Budapest Treaty for the International Recognition of the Deposit of Microorganisms for the Purposed of Patent Procedure. All restrictions on the availability of the materials deposited will be irrevocably removed upon the issuance of a patent thereon.

| | |
|---|---|
| *Xanthomonas campestris,* X59m31 | 55653 |
| *Escherichia coli* DH5α, pRK311-S88c1 | 69732 |
| *E. coli* DH5α, pRK311-NWc1 | 69733 |
| *E. coli* DH5α, PRK311-S88c2 | 69734 |
| *Sphingomonas sp.* S88#78, pRK311-S88c3 | 69735 |
| *Sphingomonas sp.* S60 pRK311-S60c2 | 69744 |

It is to be understood that the examples and embodiments described hereinabove are for the purposes of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

We claim:

1. A biologically pure culture of a Sphingomonas microorganism ATCC 69735.

2. A method of engineering a bacterium derived from a strain of Sphingomonas sp. to be a hyperproducer of sphingan polysaccharide comprising:
   isolating a DNA sequence from DNA of donor sphingan-producing bacteria selected from the group consisting of Sphingomonas sp., with the exception of ATCC 31461, ATCC 31554 and ATCC 53272; and inserting said DNA sequence into a recipient Sphingomonas sp. bacterium in multiple copies to produce a hyperproducing bacterium of sphingan polysaccharide relative to said recipient bacterium under identical fermentation conditions.

3. The method according to claim 2 wherein said recipient bacterium into which said DNA sequence is inserted is a member of a strain of Sphingomonas selected from the group consisting of ATCC31554, ATCC31461, ATCC31853, ATCC21423, ATCC31555, ATCC31961, ATCC53159 and ATCC53272.

4. The method according to claim 3 wherein said recipient bacterium into which said DNA sequence is inserted is a member of a strain of Sphingomonas selected from the group consisting of ATCC31554, ATCC31461 and ATCC53272.

5. The method according to claim 2 wherein said sphingan is S-130, or S-194.

6. A method of enhancing the production of sphingan in a Sphingomonas bacterium comprising:

1). isolating a DNA sequence from a strain of donor sphingan-producing bacteria selected from the group consisting of Sphingomonas sp. with the exception of ATCC 31461, ATCC 31554 and ATCC 53272;

2). incorporating said isolated DNA sequence from step 1 in multiple copies into a recipient Sphingomonas bacterium, resulting in said recipient bacterium becoming a hyperproducer of sphingan polysaccharide;

3). culturing the bacterium from step 2 in a fermentation broth to produce sphingan; and 4). isolating the sphingan from step 3.

7. The method according to claim 6 wherein said bacterium into which said DNA sequence is incorporated is a member of a strain of Sphingomonas selected from the group consisting of ATCC31554, ATCC31461, ATCC31853, ATCC21423, ATCC31555, ATCC31961, ATCC53159 and ATCC53272.

8. The method according to claim 7 wherein said bacterium in to which said DNA sequence is incorporated is a member of a strain of Sphingomonas selected from the group consisting of ATCC31554, ATCC31461 and ATCC53272.

9. The method according to claim 6 wherein said DNA sequence is isolated from a strain of Sphingomonas selected from the group consisting of ATCC31853, ATCC21423, ATCC31555, ATCC31961 and ATCC53159.

10. The method according to claim 6 wherein said sphingan is S-130 or S-194.

* * * * *

```
SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
          (A) LENGTH: 470 amino acids
          (B) TYPE: amino acid
```

(C) STRANDEDNESS: unknown
        (D) TOPOLOGY: unknown (ii) MOLECULE TYPE: protein (xi) SEQUENCE DESCRIPTION: SEQ ID NO:1:

Met Asn Ala Phe Glu Ala Gln Arg Ala Phe Glu Gln Leu Arg Ala
1               5                  10                  15

His Ala Arg Ser Ala Pro Ser Ala Ala Pro Met Leu Arg Arg Ser Thr
            20                  25                  30

Ile Arg Met Ile Leu Tyr Thr Glu Leu Leu Leu Asp Ser Ile Ala
            35                  40                  45

Ile Leu Leu Gly Phe Tyr Ile Ala Ala Cys Ser Arg Asp Gly Asn Trp
50                  55                  60

Leu Ser Leu Ala Gly Val Asn Val Gly Ile Phe Leu Leu Pro Ile Thr
65                  70                  75                  80

Leu Gly Thr Ala Leu Ala Ser Gly Thr Tyr Ser Leu Ser Cys Leu Arg
            85                  90                  95

Tyr Pro Val Ser Gly Val Lys Ser Ile Phe Ser Ala Phe Phe Phe Ser
            100                 105                 110

Val Phe Ile Val Leu Leu Gly Ser Tyr Leu Leu Thr Ala Glu Leu Pro
        115                 120                 125

Leu Ser Arg Leu Gln Leu Gly Glu Gly Val Leu Leu Ala Leu Ser Leu
130                 135                 140

Val Thr Ile Cys Arg Leu Gly Phe Arg Trp His Val Arg Ala Leu Thr
145                 150                 155                 160

Arg Gly Thr Leu Leu Asp Glu Leu Val Ile Val Asp Gly Val Ala Leu
            165                 170                 175

Glu Val Ala Ser Gly Ala Val Ala Leu Asp Ala Arg Ile Ile Asn Leu
            180                 185                 190

Thr Pro Asn Pro Arg Asp Pro Gln Met Leu His Arg Leu Gly Thr Thr
            195                 200                 205

Val Val Gly Phe Asp Arg Val Val Ala Cys Thr Glu Glu His Arg
210                 215                 220

Ala Val Trp Ala Leu Leu Leu Lys Gly Met Asn Ile Lys Gly Glu Ile
225                 230                 235                 240

Leu Val Pro Gln Phe Asn Ala Leu Gly Ala Ile Gly Val Asp Ser Tyr
            245                 250                 255

Glu Gly Lys Asp Thr Leu Val Val Ser Gln Gly Pro Leu Asn Met Pro
            260                 265                 270

Asn Arg Ala Lys Lys Arg Ala Leu Asp Leu Leu Ile Thr Val Pro Ala
            275                 280                 285

Leu Val Ala Leu Ala Pro Leu Met Ile Val Val Ala Ile Leu Ile Lys
            290                 295                 300

Leu Glu Ser Pro Gly Pro Val Phe Phe Ala Gln Asp Arg Val Gly Arg
305                 310                 315                 320

Gly Asn Arg Leu Phe Lys Ile Leu Lys Phe Arg Ser Met Arg Val Ala
                325                 330                 335

Leu Cys Asp Ala Asn Gly Asn Val Ser Ala Ser Arg Asp Asp Arg
            340                 345                 350

Ile Thr Lys Val Gly Arg Ile Ile Arg Lys Thr Ser Ile Asp Glu Leu
            355                 360                 365

Pro Gln Leu Leu Asn Val Leu Arg Gly Asp Met Ser Val Val Gly Pro
370                 375                 380

```
Arg Pro His Ala Leu Gly Ser Arg Ala Ala Asn His Leu Phe Trp Glu
385                 390                 395                 400

Ile Asp Glu Arg Tyr Trp His Arg His Thr Leu Lys Pro Gly Met Thr
            405                 410                 415

Gly Leu Ala Gln Ile Arg Gly Phe Arg Gly Ala Thr Asp Arg Arg Val
                420                 425                 430

Asp Leu Thr Asn Arg Leu Gln Ala Asp Met Glu Tyr Ile Asp Gly Trp
            435                 440                 445

Asp Ile Trp Arg Asp Val Thr Ile Leu Phe Lys Thr Leu Arg Val Ile
450                 455                 460

Val His Ser Asn Ala Phe
465                 470

(2) INFORMATION FOR SEQ ID NO:2:

(i) SEQUENCE CHARACTERISTICS:
         (A) LENGTH: 1950 base pairs
         (B) TYPE: nucleic acid
         (C) STRANDEDNESS: unknown
         (D) TOPOLOGY: unknown (ii) MOLECULE TYPE: DNA (genomic)

(xi) SEQUENCE DESCRIPTION: SEQ ID NO:2:

AGCCCGAATG CTGCATCCGC GAAGTGACTT TCGCCAAAGC AGCTATAGGA TGGCCCGGGG      60

CTTGATTGCC GCCGTGCGAT CAGCATAAGC GATCCATGGT CGCCAAAATC TGTCATCCTT    120

GGTAACAATC ATGCAGCCGC TAAGGAAGAT GTGCACGTCT GACGATGCTT TCTTCCGCAC    180

CCCATGCGCC GCTGACTCTG GTAGATTGAC CGTGGCCTCC ATTGCTCATC GTCTCGAAAA    240

AGGACCCTCT GGTCGCCGCG CGGACTTCCG GGAATCGATT TGTCCCGTTA TAGTGCAATG    300

CAACAGGCCG AATCGGCCGC TGTCAGCGTG CACAATCCGT TGAGGGAGCC CGACGAGGCA    360

ATGAACGCTT TTGAAGCACA GCGCGCCTTT GAGGAGCAGC TCCGGGCCCA TGCCCGTTCT    420

GCCCCCAGCG CCGCACCCAT GCTGCGACGT TCCACGATCC GCATGATCCT CTACACCGAA    480

TTGCTGTTGC TCGACAGCAT CGCAATTCTA CTGGGGTTCT ACATCGCGGC CTGCTCGCGC    540

GACGGCAACT GGCTGTCCCT TGCGGGCGTC AATGTCGGCA TCTTCCTCCT GCCGATCACG    600

CTCGGCACCG CGCTCGCCAG CGGCACCTAT TCGCTGAGCT GCCTGCGCTA CCCGGTCAGC    660

GGGGTGAAGA GCATCTTCTC GGCGTTCTTC TTCTCGGTGT TCATCGTGCT GCTGGGCAGC    720

TACCTGCTCA CCGCGGAGCT GCCGCTGTCG CGCCTGCAGC TCGGCGAGGG CGTGCTCCTG    780

GCGCTCAGCC TGGTGACGAT CTGCCGCCTT GGCTTCCGCT GGCACGTTCG TGCGCTGACA    840

CGCGGCACGC TGCTCGACGA GCTGGTGATC GTCGACGGCG TTGCCCTGGA GGTCGCGAGC    900

GGCGCGGTCG CGCTCGATGC GCGCATCATC AACCTCACGC CCAACCCGCG CGATCCGCAG    960

ATGCTGCATC GCCTCGGCAC CACCGTGGTG GGCTTCGACC GGGTCGTCGT CGCCTGCACC   1020

GAGGAGCACC GGGCAGTATG GGCGCTGCTG CTCAAGGGCA TGAACATCAA GGGCGAGATC   1080

CTCGTCCCCC AGTTCAACGC GCTGGGCGCG ATCGGCGTCG ACTCCTATGA GGGCAAGGAC   1140

ACGCTGGTCG TGTCCCAGGG CCCGCTCAAC ATGCCGAACC GCGCAAAGAA GCGGGCGCTC   1200

GATCTGCTCA TCACCGTCCC CGCGCTGGTC GCGCTGGCGC CGCTGATGAT CGTGGTCGCG   1260

ATCCTGATCA AGCTGGAGAG CCCCGGCCCC GTCTTCTTCG CACAGGACCG CGTCGGCCGC   1320

GGCAACCGAC TGTTCAAGAT CCTCAAGTTC CGCTCGATGC GCGTTGCGCT CTGCGATGCG   1380

AACGGCAACG TCTCGGCCAG CCGCGATGAC GATCGCATCA CCAAGGTAGG CCGGATCATC   1440

CGCAAGACCA GCATCGACGA GCTGCCGCAG CTGCTCAACG TGCTGCGCGG CGACATGAGC   1500
```

```
GTCGTCGGCC CGCGCCCGCA CGCACTCGGG TCGCGCGCCG CCAACCATCT CTTCTGGGAA    1560

ATCGACGAGC GCTACTGGCA CCGCCACACG CTCAAGCCGG GCATGACGGG CCTCGCGCAG    1620

ATCCGCGGCT TCCGCGGCGC GACCGATCGC CGCGTCGATC TCACCAATCG CCTGCAGGCG    1680

GACATGGAGT ATATCGACGG CTGGGACATC TGGCGGGACG TCACCATCCT GTTCAAGACG    1740

CTGCGCGTGA TCGTGCACTC CAACGCCTTC TGATCGCGGA GGGGAGCAAC GCGAGCACCG    1800

CTTGGTGCAA GAGCATTGAC ATCCGCCCTG CTTCTGCATT TGTCATTTTA TCATTGTCGT    1860

TGCGGGCCCG CCCGCGCCAT GGGGGATTTT GAATGAAGGG TATCATCCTT GCGGGGGGCA    1920

GCGGCACGCG CCTCTACCCC GCAACGCTGT                                    1950
```